(12) United States Patent
Fiechter et al.

(10) Patent No.: US 10,166,114 B2
(45) Date of Patent: Jan. 1, 2019

(54) INTERVERTEBRAL IMPLANT WITH IMPROVED SHAPE OF THE FIXING PLATE

(71) Applicant: MEDACTA INTERNATIONAL SA, Castel San Pietro (CH)

(72) Inventors: Meinrad Fiechter, Lugano (CH); Marco Riva, Longone Al Segrino (IT); Francesco Siccardi, Vico Morcote (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 297 days.

(21) Appl. No.: 14/767,640

(22) PCT Filed: Feb. 13, 2014

(86) PCT No.: PCT/IB2014/058961
§ 371 (c)(1),
(2) Date: Aug. 13, 2015

(87) PCT Pub. No.: WO2014/125428
PCT Pub. Date: Aug. 21, 2014

(65) Prior Publication Data
US 2015/0374510 A1    Dec. 31, 2015

(30) Foreign Application Priority Data
Feb. 14, 2013    (EP) .................................... 13155247

(51) Int. Cl.
*A61F 2/44*    (2006.01)
*A61F 2/30*    (2006.01)
(Continued)

(52) U.S. Cl.
CPC ........ *A61F 2/4455* (2013.01); *A61F 2/30749* (2013.01); *A61F 2/4465* (2013.01); *A61B 17/7059* (2013.01); *A61F 2/30965* (2013.01); *A61F 2/442* (2013.01); *A61F 2002/2835* (2013.01); *A61F 2002/304* (2013.01);
(Continued)

(58) Field of Classification Search
CPC ...... A61F 2/4455; A61F 2/446; A61F 2/4465; A61F 2/447; A61F 2/4611
See application file for complete search history.

(56) References Cited

U.S. PATENT DOCUMENTS

| | | |
|---|---|---|
| 5,683,394 A | 11/1997 | Rinner |
| 6,156,037 A | 12/2000 | Lehuec et al. |

(Continued)

FOREIGN PATENT DOCUMENTS

| | | |
|---|---|---|
| CN | 1053004 | 7/1991 |
| CN | 101068513 | 11/2007 |

(Continued)

*Primary Examiner* — Matthew Lawson
(74) *Attorney, Agent, or Firm* — Allen, Dyer, Doppelt + Gilchrist, P.A.

(57) ABSTRACT

An intervertebral implant (100) for the fusion between two vertebral bodies of a vertebral column comprising: —a fusion cage (1), extending from a posterior side to an anterior side, adapted to be interposed between two adjacent vertebral bodies of a patient; —an asymmetrical fixing plate (2), attached to the fusion cage (1) and having a plurality of passageways (16; 7) for the insertion of bone screws on a single side.

14 Claims, 5 Drawing Sheets

(51) Int. Cl.
  *A61B 17/70* (2006.01)
  *A61F 2/28* (2006.01)
(52) U.S. Cl.
  CPC ............ *A61F 2002/3008* (2013.01); *A61F 2002/30365* (2013.01); *A61F 2002/30367* (2013.01); *A61F 2002/30383* (2013.01); *A61F 2002/30387* (2013.01); *A61F 2002/30393* (2013.01); *A61F 2002/30395* (2013.01); *A61F 2002/30398* (2013.01); *A61F 2002/30401* (2013.01); *A61F 2002/30426* (2013.01); *A61F 2002/30492* (2013.01); *A61F 2002/30507* (2013.01); *A61F 2002/30509* (2013.01); *A61F 2002/30517* (2013.01); *A61F 2002/30578* (2013.01); *A61F 2002/30604* (2013.01); *A61F 2002/30607* (2013.01); *A61F 2002/30616* (2013.01); *A61F 2002/30774* (2013.01); *A61F 2002/30777* (2013.01); *A61F 2002/30787* (2013.01); *A61F 2002/30789* (2013.01); *A61F 2002/30792* (2013.01); *A61F 2002/30794* (2013.01); *A61F 2002/30841* (2013.01); *A61F 2002/30843* (2013.01); *A61F 2002/4475* (2013.01); *A61F 2310/00023* (2013.01); *A61F 2310/00796* (2013.01)

(56) References Cited

U.S. PATENT DOCUMENTS

| | | | |
|---|---|---|---|
| 6,235,059 B1* | 5/2001 | Benezech | A61F 2/4455 606/247 |
| 6,648,715 B2 | 11/2003 | Wiens et al. | |
| 6,699,288 B2 | 3/2004 | Moret | |
| 7,172,627 B2 | 2/2007 | Fiere et al. | |
| 7,740,662 B2 | 6/2010 | Barnett et al. | |
| 2003/0135275 A1 | 7/2003 | Garcia et al. | |
| 2004/0193269 A1* | 9/2004 | Fraser | A61B 17/7059 623/17.11 |
| 2005/0159813 A1 | 7/2005 | Molz, IV | |
| 2006/0085071 A1 | 4/2006 | Lechmann et al. | |
| 2008/0051890 A1* | 2/2008 | Waugh | A61F 2/442 623/17.11 |
| 2008/0161925 A1 | 7/2008 | Brittan et al. | |
| 2008/0300634 A1 | 12/2008 | Gray | |
| 2009/0005874 A1 | 1/2009 | Fleischmann et al. | |
| 2009/0210064 A1 | 8/2009 | Lechmann et al. | |
| 2010/0030334 A1 | 2/2010 | Molz, IV | |
| 2010/0057206 A1* | 3/2010 | Duffield | A61F 2/44 623/17.16 |
| 2010/0312346 A1 | 12/2010 | Kueenzi et al. | |
| 2011/0040382 A1* | 2/2011 | Muhanna | A61F 2/4455 623/17.11 |
| 2012/0041559 A1* | 2/2012 | Melkent | A61F 2/4455 623/17.11 |
| 2012/0109313 A1 | 5/2012 | Mathieu et al. | |
| 2012/0136392 A1 | 5/2012 | Keegan et al. | |
| 2012/0143336 A1* | 6/2012 | Aflatoon | A61F 2/4465 623/17.16 |
| 2013/0053894 A1* | 2/2013 | Gamache | A61B 17/844 606/279 |
| 2013/0060337 A1* | 3/2013 | Petersheim | A61F 2/447 623/17.16 |
| 2013/0238095 A1* | 9/2013 | Pavento | A61B 17/7059 623/17.16 |
| 2013/0310937 A1 | 11/2013 | Pimenta | |
| 2013/0345814 A1* | 12/2013 | Walkenhorst | A61F 2/4465 623/17.16 |
| 2014/0107786 A1* | 4/2014 | Geisler | A61F 2/30965 623/17.16 |
| 2014/0194994 A1 | 7/2014 | Duffield et al. | |
| 2014/0214166 A1* | 7/2014 | Theofilos | A61F 2/4455 623/17.16 |

FOREIGN PATENT DOCUMENTS

| | | |
|---|---|---|
| CN | 102038563 | 5/2011 |
| EP | 0079695 | 5/1983 |
| EP | 0891169 | 1/1999 |
| EP | 1103236 A2 | 5/2001 |
| EP | 1476098 | 11/2004 |
| EP | 1589909 | 11/2005 |
| EP | 1834608 A2 | 9/2007 |
| EP | 2628466 A1 | 8/2013 |
| EP | 2628467 A1 | 8/2013 |
| FR | 2747034 | 10/1997 |
| GB | 2457673 A | 8/2009 |
| WO | 2004069106 | 8/2004 |
| WO | 2007065993 | 6/2007 |
| WO | 2408102174 A2 | 8/2008 |
| WO | 2010107692 A1 | 9/2010 |
| WO | 2013134210 A1 | 9/2013 |

* cited by examiner

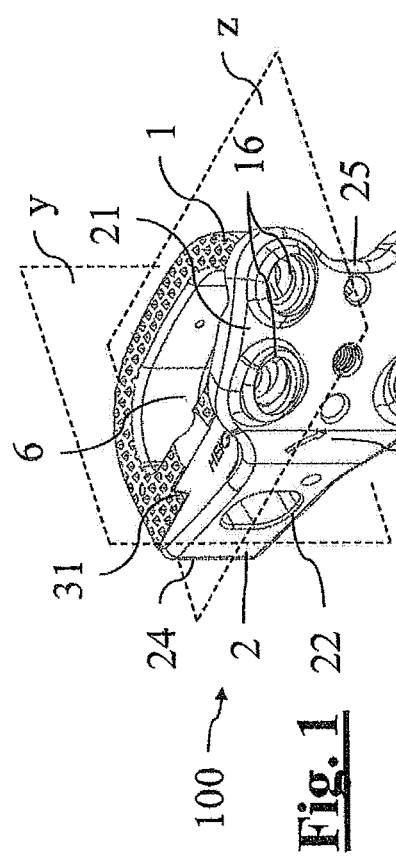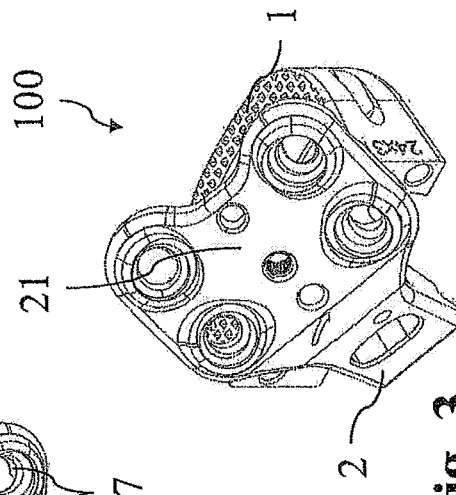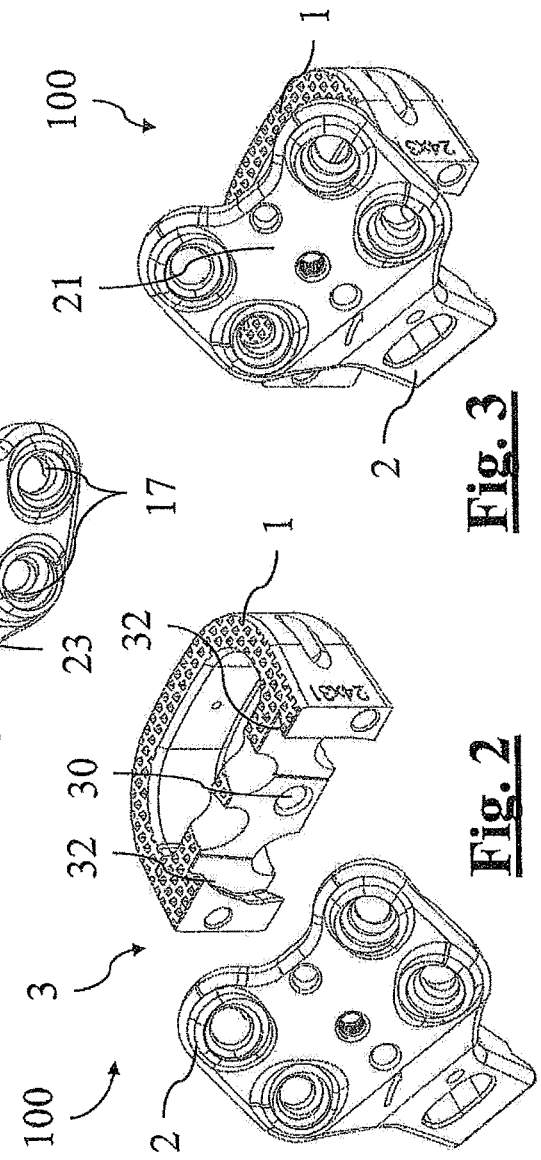

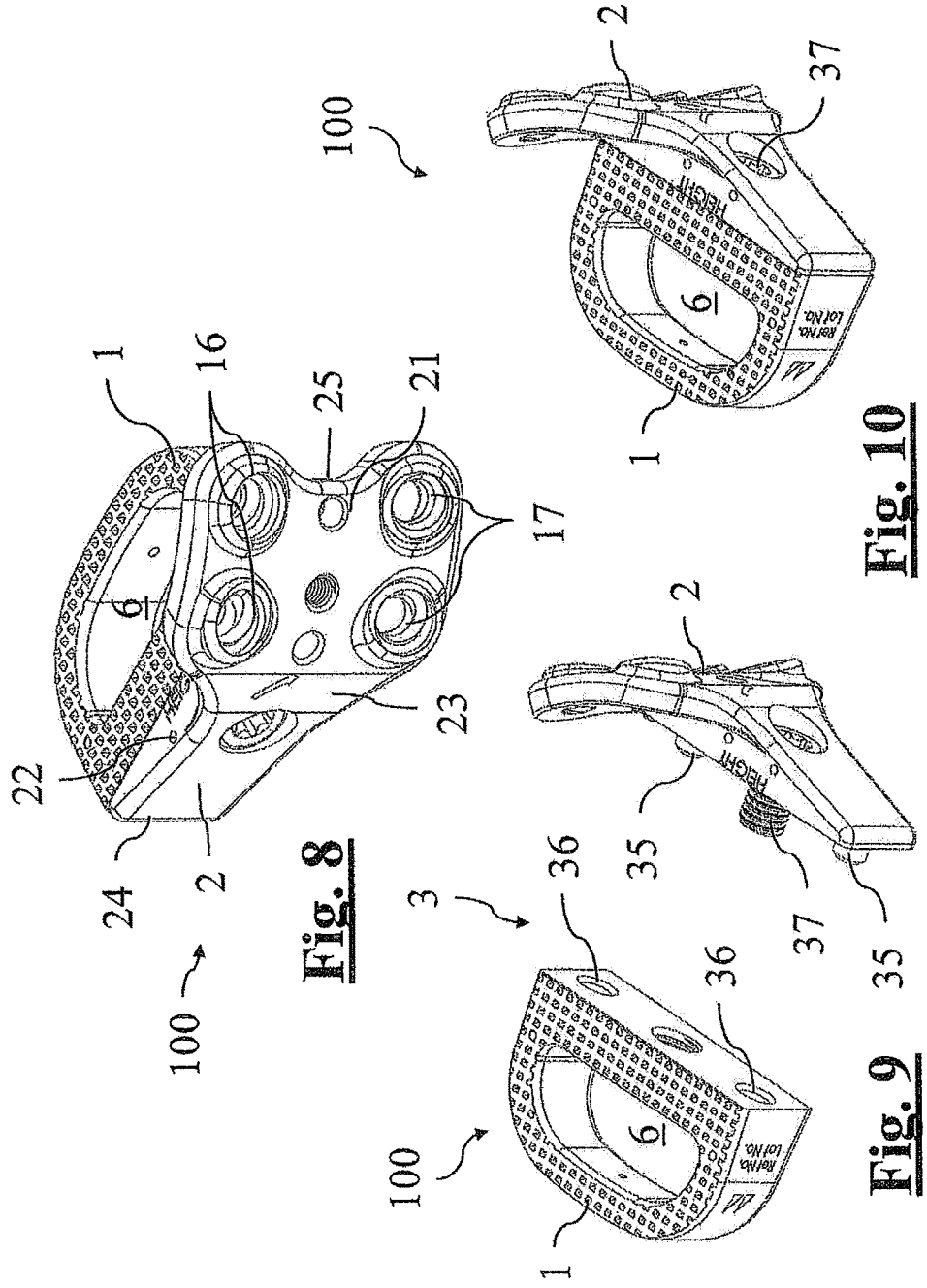

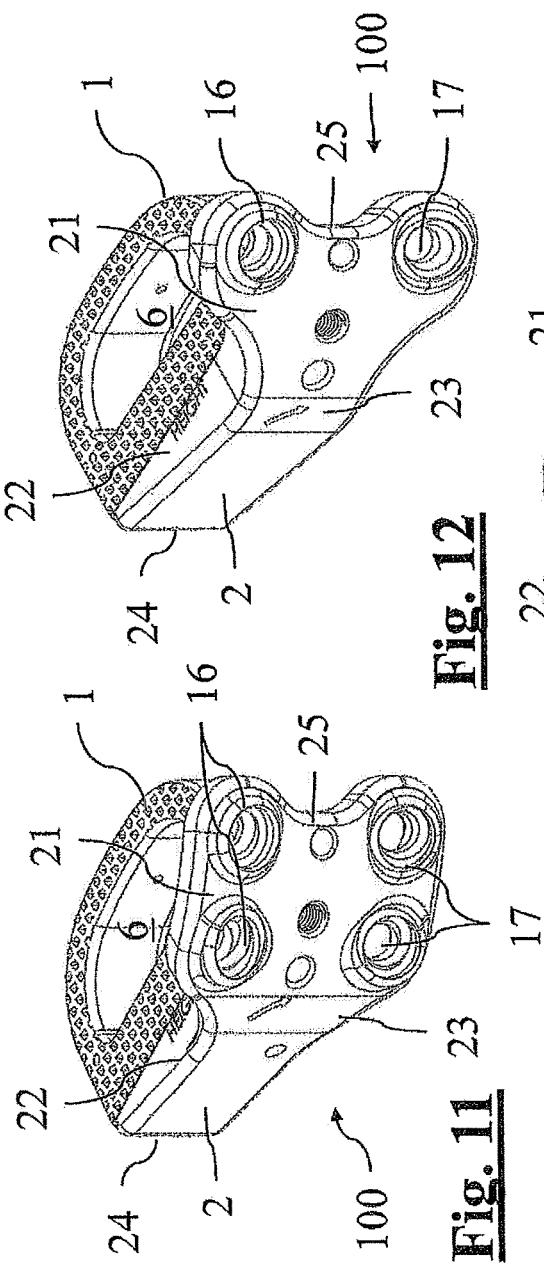
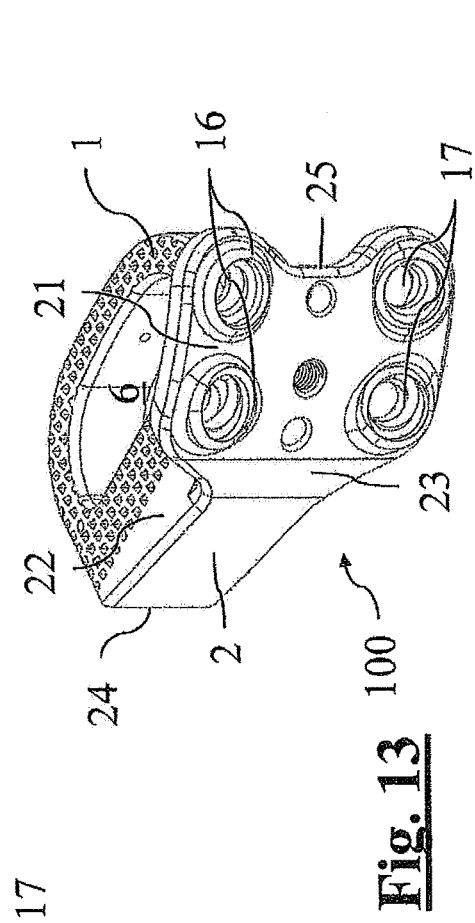
Fig. 11
Fig. 12
Fig. 13

INTERVERTEBRAL IMPLANT WITH IMPROVED SHAPE OF THE FIXING PLATE

TECHNICAL FIELD

The present invention relates to the general field of orthopedic surgical implants.

In particular, the invention relates to an intervertebral implant permitting the fusion between two vertebral bodies of a vertebral column, used in the field of surgical spine treatment.

More specifically, the implant is preferably intended to be used as stand-alone intervertebral body fusion device for Anterior Lumbar Interbody Fusion (ALIF).

BACKGROUND ART

The ALIF approach is a surgical technique mainly used to operate a damaged disk in the lumbar area of the spine. The operation involves approaching the spine through an incision in the abdomen, removing the damaged disk and substituting it with a suitable intervertebral implant.

The intervertebral implant mainly comprises a hollow cage, which is inserted between the two vertebral bodies and filled with autogenic bone graft or the like in order to promote bone growth and eventual fusion of the two bodies.

Moreover, the implant comprises a fixing plate solidly attached to the hollow cage. The fixing plate may or may not protrude out of the intervertebral space and is fixed to the anterior sides of the two adjacent vertebral bodies, usually by means of two or more bone screws. The main function of the fixing plate and screws is that of improving primal stability of the whole implant.

A drawback of the ALIF approach lies in the fact that, above the fifth lumbar vertebra, the major blood vessels are located directly in front of the spine. Therefore, the surgeon has to perform a dissection of the vessels in order to determine a surgical access for the insertion of the intervertebral plate. This preliminary operation is time-consuming and challenging.

In view of the foregoing, the technical problem underlying the present invention is to provide an intervertebral implant which can be inserted and fixed on a patient's spine above the fifth lumbar vertebra, without the need of dissecting the blood vessels.

DISCLOSURE OF THE INVENTION

The abovementioned technical problem is solved by an intervertebral implant for the fusion between two vertebral bodies of a vertebral column comprising:
  a fusion cage, extending from a posterior side to an anterior side, adapted to be interposed between two adjacent vertebral bodies of a patient; and
  a fixing plate, attached to the fusion cage (on an anterior or antero-lateral side, e.g. with an angle of 45° with respect to the anterior side) and having a plurality of passageways for the insertion of bone screws.

A median plane divides the fixing plate in two asymmetrical halves, said passageways being provided only on one of said asymmetrical halves, said passageways being inclined towards the median plane in the postero-anterior direction.

As may be readily acknowledged by a person skilled in the art, the asymmetrical shape of the intervertebral implant makes it possible for the surgeon to adopt a new operative approach. Indeed, the intervertebral implant may be inserted in an oblique direction, e.g. at 45° with respect to the mid-sagittal plane, so that no dissection of the vessels in front of the vertebrae is required. Furthermore, all the bone screw may be inserted in the passageways adopting the same surgical angle and approach.

The fixing plate may advantageously feature an enlarged lateral portion protruding in both caudal and cranial directions with respect to the height of the fusion cage, said passageways being provided on said enlarged lateral portion.

The fixing plate may advantageously feature a wedge-shaped portion on the lateral side opposite to that of the enlarged lateral portion.

Such a wedge-shaped portion is morphologically adapted to be inserted into the bone tissue of the patient, therefore easing the task of the surgeon.

The anterior surfaces of the wedge-shaped portion and of the enlarged lateral portion may advantageously converge on an anterior edge of the fixing plate, said anterior surfaces sloping in a posterior direction from said anterior edge to their lateral edges.

In order to minimize the bulk of the implant, the wedge-shaped portion may have the same height of the fusion cage.

The passageways may comprise at least an upper passageway and at least a lower passageway, symmetrically disposed with respect to a transverse plane.

In particular, the passageways may comprise two upper passageways and two lower passageways. Alternatively, the passageways may comprise only a single upper passageway and only a single lower passageway.

Preferably, the angle between said passageways and the median plane is comprised between 30° and 60°.

In an embodiment of the intervertebral implant according to the present invention, the fixing plate may be integrally formed with the fusion cage.

Alternatively, the intervertebral implant may comprise a fastening mechanism for fastening the fixing plate on the fusion cage.

The fastening mechanism may alternatively comprise: a centering pin cooperating with a centering hole along with protrusions cooperating with a rotational slideway; protrusions cooperating with a vertical slideway; protrusions cooperating with a horizontal slideway; or a plurality of centering pins cooperating with centering holes and a single fastening screw for holding the fusion cage and the fixing plate together.

Further features and advantages of the intervertebral implant according to the invention shall be made clearer by the description, given herein below, of a several embodiments described by way of non-limiting examples with reference to the accompanying drawings.

BRIEF DESCRIPTION OF DRAWINGS

FIG. 1 shows a perspective view of a first embodiment of an intervertebral implant according to the invention;

FIG. 2 shows a perspective view of the intervertebral implant of FIG. 1 with its fixing plate and fusion cage detached;

FIG. 3 shows a perspective view of the intervertebral implant of FIG. 1 in an intermediate mounting configuration;

FIG. 8 shows a perspective view of a fourth embodiment of an intervertebral implant according to the invention;

FIG. 9 shows a perspective view of the intervertebral implant of FIG. 8 with its fixing plate and fusion cage detached;

FIG. 10 shows a different perspective view of the intervertebral implant of FIG. 8;

FIG. 11 shows a perspective view of a fifth embodiment of an intervertebral implant according to the invention;

FIG. 12 shows a perspective view of a sixth embodiment of an intervertebral implant according to the invention;

FIG. 13 shows a perspective view of a seventh embodiment of an intervertebral implant according to the invention.

DETAILED DESCRIPTION OF PREFERRED EMBODIMENTS OF THE INVENTION

Figure 4:
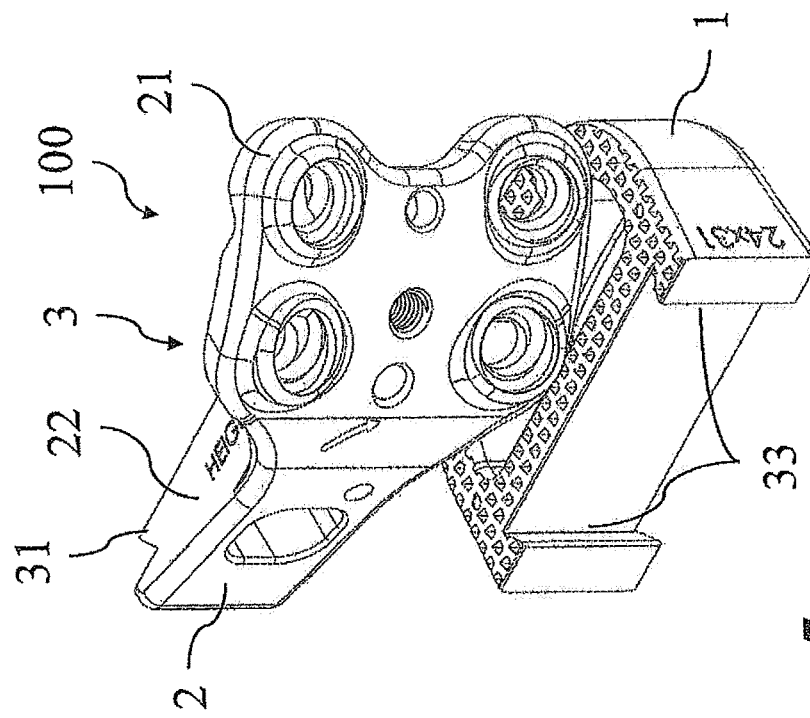
FIG. 4 shows a perspective view of a second embodiment of an intervertebral implant according to the invention.

Referring to FIGS. 1-13, with 100 is globally shown an intervertebral implant, according to several embodiments of the present invention.

It should be noted that the same reference numerals have been used to identify the elements and parts which are similar or identical, either in shape or function, in the different embodiments of the invention.

A first embodiment of the intervertebral implant 100, shown in FIGS. 1-3, comprises a fusion cage 1 coupled to a fixing plate 2 by means of a fastening mechanism globally referred as 3.

The fusion cage 1, intended to be inserted within the intervertebral space of a patient, features four walls of uniform height raising from a substantially rectangular base and enclosing a central hole 6.

The posterior side of the fusion cage 1, which is the side inserted between the vertebral bodies, exhibit rounded edges, while the anterior side, which has to be coupled with the fixing plate 2, has straight edges.

The central hole 6, extending in caudal-cranial direction, is intended to be filled with material for bone growth promotion, such as autogenic bone graft. The caudal and cranial cage surface are advantageously covered by a toothed pattern in order to improve primal stability.

The fusion cage 1 is made out of biocompatible material, for instance PEEK, CFRP or titanium, with or without a coating, for example a titanium or hydroxyapatite coating could be provided even if other coating may be used.

The fixing plate 2 has an asymmetrical structure. In order to describe its structure, two perpendicular planes should be preliminary introduced: a vertical median plane y dividing the intervertebral implant 100 in two lateral asymmetrical halves, and a transverse plane z dividing the implant in cranial and caudal roughly symmetrical halves. In particular, the vertical median plane y of the intervertebral implant divides the fusion cage in two generally symmetrical halves and the fixing plate in two asymmetrical halves.

Indeed, the fixing plate features an enlarged lateral portion 21 protruding in both caudal, cranial and lateral directions with respect to the height and width of the fusion cage 1.

Said enlarged portion 21 has four passageways 16, 17 for housing bone screws. Two upper passageways 16 are positioned on the upper side—i.e. the side protruding in cranial direction—of the enlarged portion 21; two lower passageways 17 are symmetrically placed on the lower side.

It should be noted that all passageways 16, 17 converge toward the median plane of the intervertebral implant 100.

The enlarged portion itself 21 is basically a flat tab inclined with respect to the frontal side of the fusion cage 1. In particular, the enlarged portion 21 slopes from its lateral edge 25, protruding with respect to the lateral side of the fusion cage 1, toward an anterior edge 23 of the fixing plate 2.

On the opposite side with respect to the enlarged lateral portion 21, the fixing plate 2 features a wedge-shaped portion 22 having the same height of the fusion cage 1 and sloping from the anterior edge 23 toward the lateral edge 24 of the fixing plate 2. This lateral edge 24 does not protrude with respect to the lateral side of the fusion cage 1.

The fixing plate 2 is conveniently realized with a biocompatible material, for instance PEEK, CFRP, titanium or with another alternative material suitable for implantable medical devices.

The fastening mechanism 3 provided for fastening the fixing plate 2 to the fusion cage 1 comprises a centering hole 30 of the fusion cage and a centering pin of the fixing plate 2 engaging therein. The cooperation of the two features promotes a rotation of the fixing plate 2 on the fusion cage 1; the engagement of dove-shaped protrusions 31 of the fixing plate 2 in a rotational slideway 32 defined in the fusion cage provides a further guide and a stop for said rotational mounting.

Figure 5:
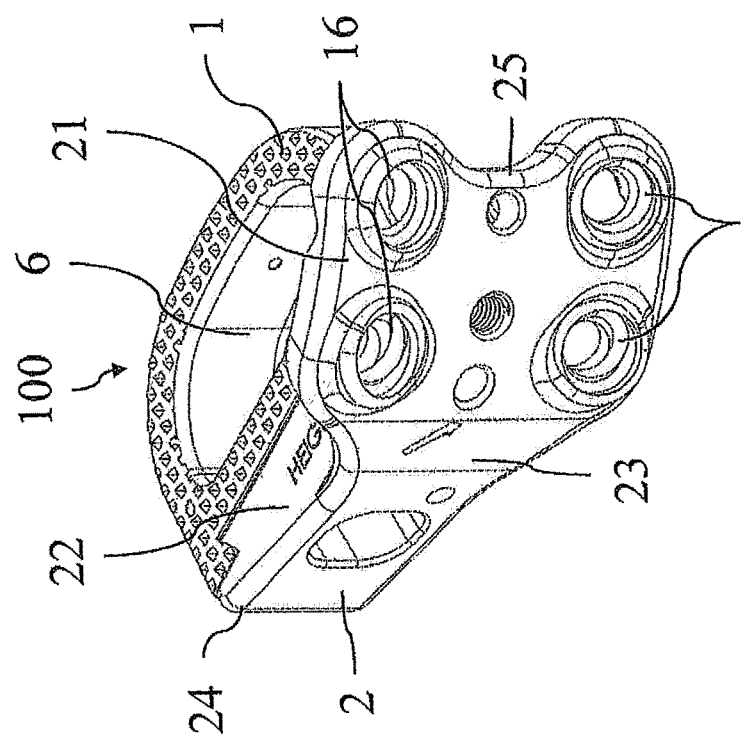
FIG. 5 shows a perspective view of the intervertebral implant of FIG. 4 with its fixing plate and fusion cage detached.

A second embodiment, depicted in FIGS. 4-5, basically shares the same features of the previously described embodiment.

However, the fastening mechanism 3 differs from the previous one in that a vertical slideway 33 substitutes the rotational slideway 32; the centering hole 30 and pin are no longer required.

Figure 6:
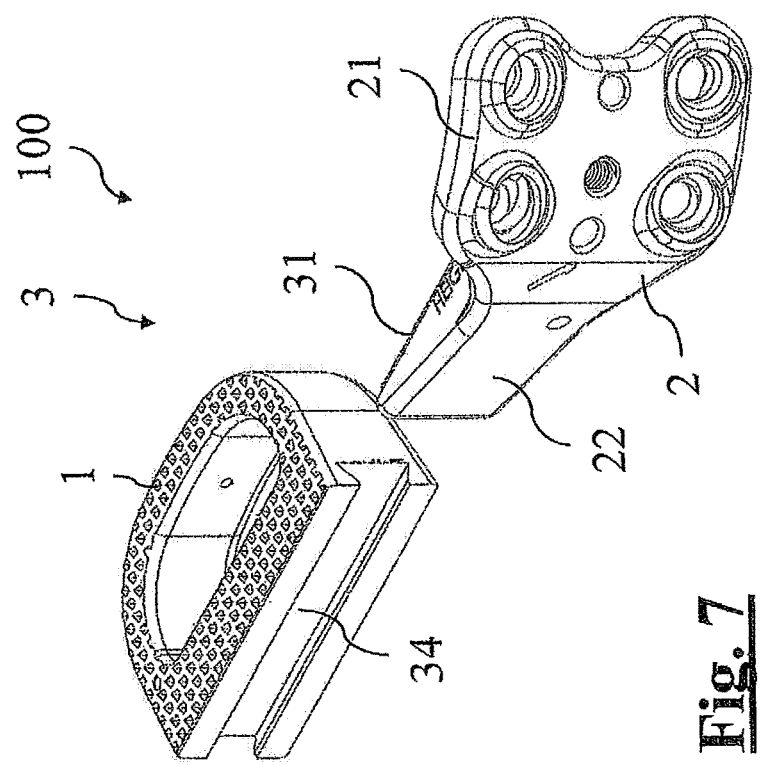
FIG. 6 shows a perspective view of a third embodiment of an intervertebral implant according to the invention.
Figure 7:
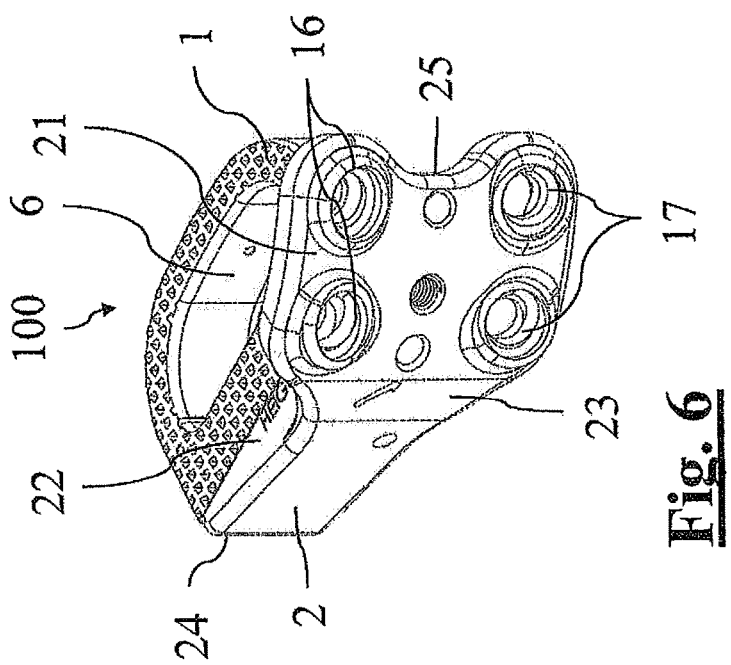
FIG. 7 shows a perspective view of the intervertebral implant of FIG. 6 with its fixing plate and fusion cage detached.

A third embodiment, depicted in FIGS. 6-7, basically shares the same features of the previously described embodiments.

Here again, the only difference lies in the fastening mechanism, which employs a horizontal slideway 34.

A fourth embodiment, depicted in FIGS. 8-10, basically shares the same features of the previously described embodiments.

Here again, a different fastening mechanism 3 is proposed. The fastening mechanism comprises two centering pins 35 housed in centering holes 36, while a single fastening screw 37 traverses the fixing plates 2 and engages in the fusion cage 1.

A fifth embodiment, depicted in FIG. 11, is substantially similar to those previously described, but differs in that the fixing plate 2 and the fusion cage 1 are preassembled. Therefore, no fastening mechanism 3 is provided.

A sixth embodiment, depicted in FIG. 12, features a slight variation in the fixing plate 2, which is provided with a single upper passageway 16 and a single lower passageway 17.

A seventh embodiment, depicted in FIG. 13, features an intervertebral implant 100 wherein the fixing plate 2 is monolithically formed with the fusion cage 1. The two elements are therefore made out of the same material. A Obviously a person skilled in the art, in order to meet specific needs, will readily acknowledge the possibility of changes and variations to the intervertebral implant described above, all comprised within the scope of protection defined by the following claims.

The invention claimed is:

1. An intervertebral implant for the fusion between two vertebral bodies of a vertebral column comprising:

a fusion cage having a posterior side extending along an arcuate path, an anterior side extending along a straight path, and first and second lateral sides each extending between the posterior and anterior sides to define a central hole, the fusion cage adapted to be interposed between two adjacent vertebral bodies of a patient;

a fixing plate, attached to the fusion cage and having a plurality of upper passageways and lower passageways for the insertion of bone screws; and a vertical median plane of the intervertebral implant dividing the fusion cage in two substantially symmetrical halves and also dividing the fixing plate in first and second generally asymmetrical halves, the first asymmetrical half secured directly to the anterior side of the fusion cage and having a height and width matching the anterior side of the fusion cage, and the second asymmetrical half extending outwardly and angularly offset from the anterior side of the fusion cage;

said plurality of upper passageways and lower passageways being provided only on said second asymmetrical half and being inclined towards the vertical median plane in the postero-anterior direction, the plurality of upper passageways being positioned above a top surface of the fusion cage, and the plurality of lower passageways being positioned below a bottom surface of the fusion cage.

2. The intervertebral implant according to claim 1, wherein the second asymmetrical half of the fixing plate has an enlarged lateral portion protruding in both caudal and cranial directions with respect to the height of the fusion cage, said plurality of upper and lower passageways being provided on said enlarged lateral portion.

3. The intervertebral implant according to claim 2, wherein the fixing plate has a wedge-shaped portion on the lateral side opposite to that of the enlarged lateral portion.

4. The intervertebral implant according to claim 2, wherein said plurality of upper and lower passageways being symmetrically disposed with respect to a transverse plane.

5. The intervertebral implant according to claim 1, wherein an angle between said passageways and the median plane is between 30° and 60°.

6. The intervertebral implant according to claim 1, wherein the fixing plate is integrally formed with the fusion cage.

7. The intervertebral implant according to claim 6, wherein the fixing plate is formed as a single component with the fusion cage.

8. The intervertebral implant according to claim 1, comprising a fastening mechanism for fastening the fixing plate on the fusion cage.

9. The intervertebral implant according to claim 8, wherein said fastening mechanism comprises a centering pin cooperating with a centering hole, and protrusions cooperating with a rotational slideway.

10. The intervertebral implant according to claim 8, wherein said fastening mechanism comprises protrusions cooperating with a vertical slideway.

11. The intervertebral implant according to claim 8, wherein said fastening mechanism comprises protrusions cooperating with a horizontal slideway.

12. The intervertebral implant according to claim 8, wherein said fastening mechanism comprises at least a fastening screw for holding the fusion cage and the fixing plate together.

13. The intervertebral implant according to claim 12, wherein the fastening mechanism comprises a single fastening screw and further comprises a plurality of centering pins cooperating with centering holes.

14. An intervertebral implant for the fusion between two vertebral bodies of a vertebral column comprising:

a fusion cage having a posterior side extending along an arcuate path, an anterior side extending along a straight path, and first and second lateral sides each extending between the posterior and anterior sides, the fusion cage adapted to be interposed between two adjacent vertebral bodies of a patient;

a fixing plate, attached to the fusion cage and having a plurality of upper passageways and lower passageways for the insertion of bone screws, the plurality of upper passageways being positioned above a top surface of the fusion cage, and the plurality of lower passageways positioned below a bottom surface of the fusion cage; and a vertical median plane of the intervertebral implant dividing the fusion cage in two generally symmetrical halves and also dividing the fixing plate in first and second substantially asymmetrical halves, the first asymmetrical half secured directly to the anterior side of the fusion cage, and the second asymmetrical half extending outwardly and angularly offset from the anterior side of the fusion cage;

said plurality of upper and lower passageways being provided only on said second asymmetrical half, said plurality of upper and lower passageways being inclined towards the vertical median plane in the postero-anterior direction;

wherein the fixing plate, attached to the fusion cage on the anterior side, has an enlarged lateral portion, contained in the second asymmetrical half in which the fixing plate is divided by the vertical median plane, said enlarged lateral portion protruding in both caudal and cranial directions with respect to a height of the fusion cage, and said plurality of upper and lower passageways being provided on said enlarged lateral portion.

* * * * *